(12) United States Patent
London et al.

(10) Patent No.: US 6,180,356 B1
(45) Date of Patent: Jan. 30, 2001

(54) MEMBRANE PORE INHIBITING AGENTS FOR TREATING INFECTION

(75) Inventors: Erwin London, Setauket, NY (US); Juanita C. Sharpe, Yeadon, PA (US)

(73) Assignee: The Research Foundation of State University of NY, Albany, NY (US)

( * ) Notice: Under 35 U.S.C. 154(b), the term of this patent shall be extended for 0 days.

(21) Appl. No.: 09/036,510

(22) Filed: Mar. 6, 1998

(51) Int. Cl.[7] .................... G01N 33/53; G01N 33/554

(52) U.S. Cl. ................ 435/7.2; 435/7.1; 435/7.32; 435/7.7; 435/7.9; 435/7.93

(58) Field of Search ................. 435/7.1, 7.2, 7.32, 435/7.7, 7.9, 7.93

(56) References Cited

PUBLICATIONS

London, "The Mechanism of Diphtheria Toxin Translocation Across Membranes," *Membrane Protein Transport*, 1:201–227 (1995).

Wang et al., "Identification of Shallow and Deep Membrane–penetrating Forms of Diphtheria Toxin T Domain That Are Regulated by Protein Concentration and Bilayer Width," *J. Biol.Chem.*, 272:25091–25098 (1997).

Stegmann et al., "Protein–Mediated Membrane Fusion," *Annu. Rev. Biophys. Chem.*, 18:187–211 (1989).

Pappenheimer, "Diphtheria Toxin," *Ann. Rev. Biochem.*, 46:69–94 (1977).

Gordon et al., "Proteolytic Activation of Bacterial Toxins by Eukaryotic Cells Is Performed by Furin and by Additional Cellular Proteases," *Infection and Immunity*, 63:82–87 (1995).

London, "Diphtheria toxin: membrane interaction and membrane translocation," *Biochim.Biophys. Acta*, 1113:25–51 (1992).

Collier, "Structure and Activity of Diphtheria Toxin," in *ADP–Ribosylation Reactions: Biology and Medicine*, Academic Press, NY, pp. 575–592 (1982).

Mindell et al., "Structure–Function Relationships in Diphtheria Toxin Channels: III. Residues which Affect the Cis pH Dependence of Channel Conductance," *J. Membrane Biol.* 137:45–57 (1994).

Jiang et al., "Characterization of Diphtheria Toxin–Induced Lesions in Liposomal Membranes," *J. Biol. Chem.*, 264:13424–13429 (1989).

Kagan et al., "Diphtheria toxin fragment forms large pores in phospholipid bilayer membranes," *Proc. Natl. Acad. Sci. USA*, 78:4950–4954 (1981).

Donovan et al., "Diphtheria toxin forms transmembrane channels in planar lipid bilayers," *Proc. Natl. Acad. Sci. USA*, 78:172–176 (1981).

Falnes et al., "Replacement of Negative by Positive Charges in the Presumed Membrane–inserted Part of Diphtheria Toxin B Fragment," *J. Biol. Chem.*, 267:12284–12290 (1992).

(List continued on next page.)

*Primary Examiner*—Ali Salimi
(74) *Attorney, Agent, or Firm*—Hoffmann & Baron, LLP

(57) ABSTRACT

The invention relates to methods for identifying antimicrobial agents which inhibit bacterial toxin membrane pore formation and for treating diseases where bacterial protein toxins that form pores in membranes are virulence agents. The invention involves screening for small molecule agents which inhibit membrane pore formation by bacterial protein toxins. The invention is also a method for treating bacterial infection by inhibiting membrane pore formation by bacterial toxin using agents that inhibit membrane pore formation by bacterial toxins. The methods of the invention are also applicable for developing antiviral agents that treat viral infection where exposure of hydrophobic sites of proteins is associated with infection.

24 Claims, 9 Drawing Sheets

OTHER PUBLICATIONS

Silverman et al., "Mutational Analysis of the Helical Hairpin Region of Diphtheria Toxin Transmembrane Domain," *J. Biol. Chem.*, 269:22524–22432 (1994).

Antoni et al., "Purification of diphtheria toxin by chromatography on Cibacron Blue–Sepharose," *Experientia*, 39:885–886 (1983).

Rambelli et al., "Interaction of Diphtheria Toxin Fragment A and of Elongation Factor 2 with Cibacron Blue," *Bioscience Reports*, 7:737–743 (1987).

Moskaug et al., "Low pH–induced Release of Diphtheria Toxin A–fragment in Vero Cells," *J. Biol. Chem.*, 263:2518–2525 (1988).

Falnes et al., "Cell–mediated Reduction and Incomplete Membrane Translocation of Diphtheria Toxin Mutants with Internal Disulfides in the A Fragment," *J. Biol. Chem.*, 270:20787–20793 (1995).

Jiang et al., "Self–translocation of Diphtheria Toxin across Model Membranes," *J. Biol. Chem.*, 266:24003–24010 (1991).

Zhao et al., "Conformation and Model Membrane Interactions of Diphtheria Toxin Fragment A," *J. Biol. Chem.*, 263:15369–15377 (1988).

Ren et al., "Transmembrane Orientation of Hydrophobic α–Helices Is Regulated Both by the Relationship of Helix Length to Bilayer Thickness and by the Cholesterol Concentration," *Biochemistry*, 36:10213–10220 (1997).

Tobkes et al., "Secondary Structure and Assembly Mechanism of an Oligomeric Channel Protein," *Biochemistry*, 24:1915–1920 (1985).

Menestrina et al., "Lipid interaction of *Pseudomonas aeruginosa* exotoxin A: Acid–triggered permeabilization and aggregation of lipid vesicles," *Biophys. J.*, 60:1388–1400.

Blaustein et al., "Anthrax toxin: Channel–forming activity of protective antigen in planar phospholipid bilayers," *Proc. Natl. Acad. Sci. USA*, 86:2209–2213 (1989).

Hoch et al., "Channels formed by botulinum, tetanus, and diphtheria toxins in planar lipid bilayers: Relevance to translocation of proteins across membranes," *Proc. Natl. Acad. Sci. USA*, 82:1692–1696 (1985).

Lesieur et al., "Membrane insertion: the strategies of toxins (Review)," *Molecular Membrane Biology*, 14:45–64 (1997).

Valeva et al., "Staphylococcal α–Toxin: Formation of the Heptameric Pore Is Partially Cooperative and Proceeds through Multiple Intermediate Stages," *Biochemistry*, 36:13298–13304 (1997).

London, "How bacterial protein toxins enter cells: the role of partial unfolding in membrane translocation," *Molecular Microbiology*, 6:3277–3282 (1992).

Bayley, "Toxin structure: Part of a hole?," *Current Biology*, 7:R763–R767 (1997).

Rey et al., "The envelope glycoprotein from tick–borne encephalitis virus at 2 Å resolution," *Nature*, 375:291–298 (1995).

White et al., "Membrane fusion proteins of enveloped animal viruses," *Quarterly Reviews of Biophysics*, 16:151–195 (1983).

McKeever et al., "Preliminary Crystallographic Investigation of the Protein Toxin from *Corynebacterium diphtheriae*," *J. Biol. Chem.*, 257:6923–6925 (1982).

Carroll et al., "Dimeric Form of Diphtheria Toxin: Purification and Characterization," *Biochemistry*, 25:2425–2430 (1986).

Silverman et al., "Structure–Function Relationships in Diphtheria Toxin Channels: I. Determining a Minimal Channel–Forming Domain," *J. Membrane Biol.*, 137:17–28 (1994).

Zhan et al., "Dynamic Transitions of the Transmembrane Domain of Diphtheria Toxin: Disulfide Trapping and Fluorescence Proximity Studies," *Biochemistry*, 33:11254–11263 (1994).

MEMBRANE PORE INHIBITING AGENTS FOR TREATING INFECTION

This invention was made with Government support under Grant No. GM 31986 awarded by the National Institutes of Health. The Government has certain rights in the invention.

The present invention relates to methods for developing drugs for treating bacterial and viral infections. More specifically, the invention relates to screening for, developing, and using small molecule agents which inhibit pore formation in membranes by bacterial protein toxins.

BACKGROUND OF THE INVENTION

Many bacteria secrete protein toxins which form pores in host membranes as part of their infective cycle. Examples include *Corynebacterium diphtheriae, Pseudomonas aeruginosa, Bacillus anthracis,* and *Staphylococcus aureus*. In many cases these secreted toxins are necessary for or are associated with bacterial virulence. For example, *Corynebacterium diphtheriae* is only virulent if it secretes diphtheria toxin. (see Pappenheimer, A. M., Jr., *Annu. Rev. Biochem.* 46, 69–94 (1977)). In addition, these toxins often cause tissue damage.

Diphtheria toxin is illustrative of the membrane pore forming bacterial toxins. This toxin is secreted as a single polypeptide (Mr 58,348), but can be readily cleaved by a furin-like protease into two subunits, A (Mr 21,167) and B (Mr 37,199), which are held together by a disulfide bond. Diphtheria toxin enters cells by receptor-mediated endocytosis, and, once internalized, the acidification of the endosomal lumen triggers a pH dependent conformational change which causes the toxin to become hydrophobic and penetrate the endosomal membrane. See Gordon, V. M., et al., *Infect. Immun.* 63, 82–87 (1995) and London, E., *Biochim. Biophys. Acta* 1113, 25–51 (1992). After reduction of the disulfide bond holding the A and B subunits together, the A chain is translocated across the membrane bilayer into the cytoplasm where it catalyzes the ADP-ribosylation of elongation factor 2, inhibiting protein synthesis and causing cell death. See, for example, Collier, R. J. in ADP Ribosylation reactions: Biology and Medicine (Hayashi, O. and Ueda, K., eds.) pp. 573–592 (1982), Academic Press, New York.

The mechanism of A chain translocation across membranes involves pore formation. For example, see Mindell, J. A., et al. *J. Memb. Biol.* 137, 45–57 (1994); Jiang, G.-S., et al. *J.Biol.Chem.* 264, 13424–13429 (1989); Kagan, B. L., et al. *Proc. Natl.Acad.Sci. USA* 78, 4950–4954 (1981); and Donovan, J. J., et al. *Proc.Natl.Acad. Sci. USA* 78, 172–176 (1981). Significantly, using mutant toxins, it has been shown that membrane pore formation by the toxin is associated with its translocation and toxicity. See Falnes, P. O., et al. *J.Biol.Chem.* 267, 12284–12290 (1992); and Silverman, J. A., et al. *J.Biol.Chem.* 269, 22524–22532 (1994).

While bacterial infections are usually treated with antibiotics which destroy bacteria and/or interfere with bacterial growth, resistance to standard antibiotics is an increasingly serious problem. Moreover, for bacterial infections involving toxin production, using antibiotics after symptoms have manifested will often be too late because considerable toxin production will already have occurred, and antibiotics are not effective against toxins.

In cases where toxin production has already occurred, antitoxins have been used. However, since these antitoxins are antibodies, they only bind to toxin in the circulatory system and cannot act on toxins which have already been internalized into cells. Antitoxins currently used are animal products in which contamination by pathogens (including virus) can occur. Moreover, antitoxins are unstable, have a limited shelf life, and must be stored under refrigeration. Antitoxins must also be administered by injection. These disadvantages have greatly limited the use of antitoxins and there is a need for new therapeutic approaches to this problem.

Cibacron dyes have been shown to bind to the catalytic (enzymatic) site of diphtheria toxin at neutral pH, i.e. when the toxin is not in the conformation that inserts in membranes. See, for example, Antoni, G., et al., *Experiential* 39, 885–886 (1983); Rambelli, F., et al., *Bioscience Reports*, 7, 737–743 (1987). Diphtheria toxin enzymatic activity occurs at a step in the infective cycle after pore formation. There is no suggestion that Cibacron dyes or any other molecules affect pore formation.

Cibacron blue, and other molecules with similar chemical moieties, have been shown to affect diphtheria toxin translocation across Vero cell membranes. For example, Moskaug, J. O., et al., *J.Biol.Chem.* 263, 2518–2525 (1988), found that DIDS, an inhibitor of anion transport, blocks the translocation of the A fragment of diphtheria toxin across cell membranes and reduces the insertion of a 25 kDa fragment of the protein into cell membranes. From these results, the authors concluded that either anion transport is necessary for toxin translocation across the membrane or that an anion transporter might be a receptor for the toxin. No suggestion that DIDS affects pore formation was made. An article by Falnes, P. Ø., and Olsnes, S., *J.Biol.Chem.* 270, 20787–20793 (1995), discloses DIDS, NEM, and Cibacron blue as inhibitors of diphtheria toxin translocation across Vero cell membranes. This article teaches that Cibacron Blue and DIDS disrupt translocation by inhibiting anion transport. NEM is hypothesized to act by quenching cellular reducing agents. Inhibition of pore formation is not suggested.

None of the references cited above teach or suggest that the molecules described therein, or any other molecules, inhibit membrane pore formation by protein toxins. Nor do these references teach or suggest methods for developing pharmaceuticals whose mechanism of action is the inhibition of membrane pore formation by protein toxins.

In view of the above considerations, it is clear that methods for reducing the effects of toxins and of treating bacteria harboring toxins have been limited. Accordingly, it is one of the purposes of the present invention to overcome these limitations in treatment of infections where the mechanism of virulence involves membrane pore formation by protein toxins. The invention provides methods for obtaining agents that are effective at inhibiting pore formation in membranes by protein toxins.

SUMMARY OF THE INVENTION

Accordingly, a new method has now been discovered to identify and develop antimicrobial agents which inhibit pore formation in membranes by bacterial protein toxins. The present invention is also a method to treat bacterial infections by inhibition of pore formation by bacterial protein toxins.

In a preferred embodiment, the invention is a method for identifying antimicrobial agents which inhibit bacterial toxin membrane pore formation comprising contacting a membrane pore-forming toxin protein with a target agent in the presence of a membrane, under conditions in which the toxin protein forms pores in the membrane; measuring the extent of pore formation in the membrane; and comparing the extent of pore formation to that obtained in the absence of the target agent, wherein significant inhibition of pore formation by the target agent constitutes identifying an antimicrobial agent.

Preferably the membrane is a biological membrane, and more preferably the membrane is in the form of a vesicle that can trap a reporter group. A preferred embodiment of the invention determines the extent of pore formation by measuring the passing of a reporter group through the membrane. Preferably the reporter group is fluorescent and pore formation is determined by the quenching of the fluorescent group by a quencher which acts upon the fluorescent groups passing through the membrane. The extent of pore formation can be assessed by the size of the fluorescent reporter group that can pass through the membrane pores, and/or the amount of a reporter group of a fixed size that is released.

In a preferred embodiment, the invention is a method for identifying antimicrobial agents which inhibit bacterial toxin membrane pore formation comprising preparing an aqueous solution, in which bacterial toxin can form pores in membranes, of phospholipid vesicles which contain fluorescent reporter in the lumen. Then introducing target agent and pore forming toxin to the solution, incubating, and then measuring the fluorescence of the solution. Quencher is then introduced into the solution and the fluorescence of the solution is again measured to determine the quenching of the fluorescent reporter that has passed through the membrane, and thus assaying pore formation in the membrane.

Preferably the fluorescent reporter is 8-hydroxypyrene-1, 3,6-trisulfonic acid labeled dextran. A preferred quencher is anti 8-hydroxypyrene-1,3,6-trisulfonic acid antibodies.

In yet another preferred embodiment, the invention is a method for identifying antimicrobial agents which inhibit bacterial toxin membrane pore formation comprising preparing an aqueous solution, in which bacterial toxin can form pores in membranes, of phospholipid vesicles which contain quencher in the lumen; introducing target agent and pore forming toxin to the solution and incubating; introducing fluorescent reporter to the solution; and measuring fluorescence of the solution and comparing that fluorescence to the fluorescence of a similar sample lacking toxin to determine the quenching of the fluorescent reporter that has passed through the membrane, and thus assaying pore formation in the membrane.

Once again in this embodiment of the invention, preferably the fluorescent reporter is 8-hydroxypyrene-1,3,6-trisulfonic acid labeled dextran. A preferred quencher is anti 8-hydroxypyrene-1,3,6-trisulfonic acid antibodies.

Antimicrobial agents selected can than be applied to cultured cells to which a membrane pore forming toxin has been added. The increase in cell survival due to the addition of the pore inhibiting antimicrobial can then be assayed.

Another embodiment of the invention is a method for treating bacterial infection by inhibiting toxin induced membrane pore formation. The inhibition of pore formation can by carried out by contacting toxin or a toxin-bearing cell with agents that inhibit pore formation.

Preferred agents that inhibit membrane pore formation by bacterial toxins are polycyclic amphipathic molecules that contain at least two aromatic groups and at least two sulfonic acid groups attached as substituents of the aromatic groups. Other negatively charged molecular moieties or groups of similar charge density can be used in place of sulfonic acid. Ring members are primarily C but can include N and other heteroatoms. Substituents to the aromatic groups other than sulfonic acid groups can include OH, $NH_2$, Cl, and other such groups. Molecules such as these are also preferred target agents for the inventions methods for indentifying antimicrobial agents which inhibit bacterial toxin membrane pore formation.

The agents that inhibit pore formation can be administered in the presence of antibiotic and antitoxin.

The invention can be used to treat infections caused by bacteria such as *Corynebacterium diphtheriae, Pseudomonas aeruginosa, Bacillus anthracis, Staphylococcus aureus* and *Clostridium*. These infections can be in mammals, examples including humans and ruminants.

A preferred embodiment of the invention delivers agents that inhibit pore formation directly to the lungs of cystic fibrosis patients that are infected with *Pseudomonas aeruginosa*, and preferably delivers the agents to the lungs in the form of an inhalation aerosol.

Agents that inhibit pore formation can be administered in an uncharged form as an ester which is then hydrolyzed to the charged form when the agent is trapped in a cell.

The method of the invention can also be used to treat tissue damage associated with bacterial toxins by administering an effective dose of molecules that inhibit toxin induced membrane pore formation.

In another embodiment, the invention can be used to treat bacterial and viral infections by administering agents that inhibit the interaction of hydrophobic exposed groups of bacterial and viral proteins with membranes.

The invention has a number of significant advantages. The invention provides a method for developing small molecule drugs effective against a previously unexploited drug target. Having a target, paradigmatic drugs effective against this target, and a convenient assay to determine effectiveness of potential drugs provides a practicable approach to drug design.

Another important advantage of the present invention is that the drugs developed can, unlike previous treatment such as antitoxins, be delivered orally, topically, or as an aerosol spray. The provision of drugs that can be delivered directly to the lungs in the form of an aerosol spray is a crucial advantage for cystic fibrosis patients.

Importantly, the molecules of the invention can block the effects of toxins already internalized in cells and can close existing toxin pores. Toxins that are beyond the reach of other treatments are therefore, for the first time, susceptible to treatment and toxin induced cellular damage from toxin already internalized in cells can be prevented.

The methods of the invention provide an alternative therapy for opportunistic infections of *Pseudomonas aeruginosa* in cystic fibrosis patients. These infections have been a major threat to cystic fibrosis patient and antibiotic treatments have caused severe side effects.

These and other advantages of the present invention will be appreciated from the detailed description and examples which are set forth herein. The detailed description and examples enhance the understanding of the invention, but are not intended to limit the scope of the invention.

DETAILED DESCRIPTION OF THE INVENTION

Figure 1:
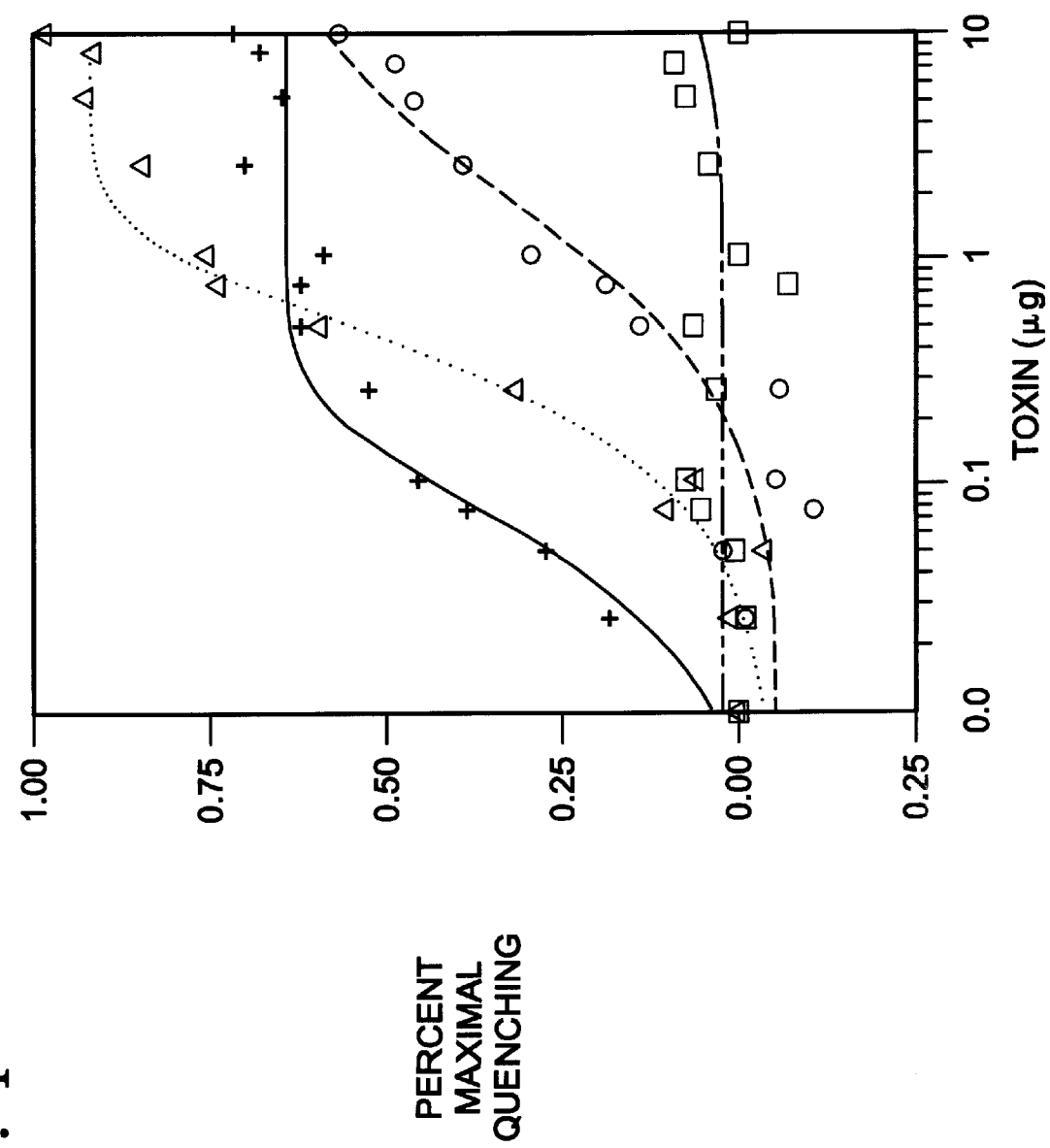
FIG. 1 describes the leakage of molecules of different sizes through pores made by diphtheria toxin as assessed by the quenching of fluorescence when the molecules leak out.

The present invention is directed to a methods for identifying and developing antimicrobial agents which inhibit pore formation in membranes by protein toxins. The invention also provides methods for treating infection by inhibiting membrane pore formation by bacterial toxins.

The invention makes use of the unexpected discovery that a group of molecules having similar chemical features inhibit membrane pore formation by diphtheria toxin. The chemically identifiable features of these molecules provide a rationale for identifying target agents which are to be tested for their capacity to inhibit membrane pore formation.

The invention is useful for developing small molecule agents (or drugs) effective at treating bacterial infections in which protein toxins make pores in host cell membranes. Drug development includes, but is not limited to, identifying molecules effective at inhibiting pore formation in membranes by bacterial protein toxins, and chemically modifying molecules found to be inhibitory to enhance their membrane pore inhibiting capacity.

Target agents can generally be described as molecules that are amphipathic, contain aromatic groups, and have anionic acid groups attached to the aromatic groups. The aromatic groups can be structures such as benzene, naphthalene, triazine compounds, anthracene, pyrene and the like. The anionic group can be a sulfonic acid groups or other anionic groups such as carboxylic acid groups or the like. Carbon (C) atoms are most commonly found as the ring members of the aromatic groups, but nitrogen (N) and other such heteroatoms can also be ring members. For example, heterocyclic aromatic groups, such as triazene, are found in some of these molecules. A commonly observed feature of these molecules is that the aromatic groups are connected to each other by one or two nitrogens. A variety of substituents can be attached to the rings, in addition to the sulfonic acid groups, such as chlorine (Cl), Hydroxyl groups (OH), Oxygen (O), and carboxyl groups. These paradigmatic features provide guidance for selecting and developing pharmaceuticals that inhibit membrane pore formation by protein toxins.

While not wishing to be bound by any one theory, it is likely that the broad physical chemical characteristics of these molecules make them effective at inhibiting pore formation by facilitating their interaction with the membrane penetrating conformation of the protein toxins such that they cannot form membrane pores. Alternatively, these molecules could bind to the membrane in such a way that they prevent toxins from interacting such that they form pores in the membrane.

Useful molecules for inhibiting membrane pore formation by bacterial toxins that share the features described above include Cibacron Blue, Cibacron Brilliant Red, 3-Hydroxy-4-[(4-sulfo-1-naphthalenyl)azo]2,7-naphthalenedisulfonic acid trisodium salt (Amaranth), 8-methoxy-pyrene 1,3,6-trisulfonic acid (MPT), 3-hydroxy-4-[2-sulfo-4(4-sulfophenylazo)phenylazo]-2,7-naphthalenedisulfonic acid (Ponceau S), Aniline Blue, Fast Green FCF, and other such molecules. Such molecules can be used as models from which potential target agents can be identified.

One embodiment of the invention is a method for identifying antimicrobial agents which inhibit bacterial toxin membrane pore formation. This method comprises contacting a membrane pore-forming toxin protein with a target agent in the presence of a membrane under conditions in which the toxin forms pores in the membrane, measuring the extent of pore formation in the membrane, and comparing the extent of membrane pore formation to that obtained in the absence of the target agent, wherein significant inhibition of membrane pore formation by the target agent constitutes identifying an antimicrobial agent.

The extent of pore formation can be assessed by the size of the reporter group that can pass through the membrane pores, and/or the amount of a reporter group of fixed size that can pass through the membrane. The extent of pore formation refers to the size of the pores and/or the number of pores in the membrane. A greater extent of pore formation means that in comparison to another membrane, there are more pores, larger pores, or both more pores and larger pores.

Significant inhibition of membrane pore formation means at least 2% Preferably, significant inhibition of membrane pore formation means at least 5%. More preferably significant inhibition of membrane pore formation means at least 10%. Even more preferably, significant inhibition of membrane pore formation means at least 40%. Optimally, significant inhibition of membrane pore formation means at least 75%.

Conditions under which the protein toxin forms pores in membranes are conditions in which the protein will spontaneously form pores in membranes. For example, diphtheria toxin in a 150 mM NaCl, pH=4.5 solution forms pores in phospholipid membranes comprised of phosphatidylcholine (PC) and phosphatidylglycerol (PG).

A variety of membranes can be used with the methods of the invention. Such membranes include model membrane vesicles, cells (e.g. erythrocytes), and planar bilayers. Preferably the membrane is comprised of biological molecules. Biological molecules can include, but are not limited to, lipids, proteins and carbohydrates. A membrane Preferred membranes are lipid bilayers. The bilayer can be comprised of any lipids, but preferably the lipids are those found in biological membranes. Suitable lipids that can be used with the methods of the invention include 1,2-diacyl-sn-glycero-3-phosphocholine (PC), 1,2-diacyl-sn-glycero-3[phospho-rac-(1glycerol)] (PG), cholesterol, sphingomyelin, 1,2-diacyl-sn-glycero-3-phosphoethanolamine (PE), and the like. A wide variety of different lipids and mixtures of these lipids can be prepared and used. Lipids can be purchased from Avanti Polar Lipids (Alabaster, Al).

Preferably the membrane is in the form of a vesicle. A variety of different vesicle preparations and types of vesicles can be used with the methods of the invention. For example small unilamellar vesicles (SUVs), vesicles with a diameter of about 250 Å to about 500 Å, can be used. These vesicles can be prepared in a variety of ways, including sonication and ethanol dilution. Preferably large unilamellar vesicles (LUVs) are used with the methods of the invention. LUVs have diameters of about 500 Å to about 5000 Å. LUVs can be prepared in different ways such as freeze-thaw of SUVs, extrusion of multilamellar dispersions through polycarbonate filters, and octyl glucoside dialysis. Preferably, the LUVs are prepared by octyl glucoside dialysis. For vesicle preparations and characterization see, for example, Zhao et al. J.Biol.Chem. 263, 15369–15377 (1988); Jiang, J. X. et al., J. Biol. Chem. 266, 24003–24010 (1991); and Ren et al.

*Biochemistry* 36, 10213–10220 (1997). For an extensive discussion of vesicles and membranes, see, for example, R. B. Gennis, Biomembranes: *Molecular Structure and Function*, Springer-Verlag (1989), which is herein incorporated by reference.

Pore formation can be determined in a variety of ways. See, for example, Jiang, G.-S. et al. *J.Biol.Chem.* 264, 13424–13429 (1989); Kagan, B. L., et al. *Proc.Natl.Acad.Sci. USA* 78, 4950–4954 (1981), which are herein incorporated by reference. In a preferred embodiment of the invention, a reporter is trapped in a phospholipid, and membrane pore formation by a protein toxin is assessed by detection of the reporter group passing out of the membrane. In general, a reporter group is any molecule or substance that can be detected upon its passing through the membrane. Toxin and target agents can be added to the outside of membrane vesicles which contain a trapped reporter group, and pore formation can be assayed by recording the passing of the reporter group through the membrane. Alternatively, the pore formation can be assessed by the reporter group passing into the vesicle. The comparison of the pore formation in the presence and absence of target agents is used to determine whether significant inhibition of membrane pore formation is obtained. Preferably, the reporter group is fluorescent, and pore formation is assessed (determined) by quenching of the fluorescence of the reporter group upon its passing through a membrane pore by quenchers that are too large to pass through the pores and are present on the other side of the membrane.

Fluorescence quenching refers to a decrease in the fluorescence of a fluorescent substance in the presence of a quencher. Quenchers are substances that cause a decrease in fluorescence when they interact with fluorescent molecules. For a detailed discussion of fluorescence, fluorescence quenching, and fluorescence methods in general, see, for example, J. R. Lakowicz, *Principles of Fluorescence Spectroscopy*, Plenum Press (1983), which is herein incorporated by reference.

Cascade blue (8-hydroxypyrene-1,3,6-trisulfonic acid) labeled dextrans are preferred fluorescent reporters for use with the invention. Dextrans are polymers of glucose that can be prepared in different sizes. Cascade blue is fluorescent. Free cascade blue is 8-methoxy-pyrene-1,3,6-trisulfonic acid. Pore size can be assessed by the size of the reporter group. Any fluorescent molecule can be used as a reporter group. Fluorescent molecules can be attached to dextrans of varying sizes. Fluorescently labeled dextrans of varying sizes can be used to assess the size of pores in the membrane. For example, cascade blue labeled dextrans with molecular weights of 3 kD, 10 kD, and 70 kD can be used. Other suitable fluorescent groups that could be used as reporter groups include rhodamine, eosin, fluorescein, Lucifer yellow, Texas Red®, Oregon Green®, BODIPY® and the like (available from Molecular Probes, Eugene, Oreg.). Generally any fluorescent group that is soluble in water, and that does not pass through the membrane when no pores in the membrane are present, can be used to assess pore formation and/or size of the pores.

Many quenchers can be used to quench the fluorescence of fluorescent reporter groups. Preferred quenchers for the method of the invention are anti-cascade blue antibodies which quench the fluorescence of cascade-blue labeled dextrans. Other quenchers can be used depending on the fluorescent reporter chosen.

By aqueous, we mean a solution that is predominantly water. Such solutions can contain salts and buffers so that the ionic strength and pH are compatible with protein toxin membrane pore formation.

Another embodiment of the invention is a method for treating bacterial infection by inhibiting toxin induced membrane pore formation. Inhibition of toxin induced membrane pore formation can be accomplished by contacting either toxin or toxin-bearing cells with agents that inhibit membrane pore formation by bacterial protein toxin. A general description of agents that inhibit toxin induced membrane pore formation useful with this embodiment of the invention can be found above under the description of target agents. Molecules that have been found to inhibit membrane pore formation by bacterial protein toxins are useful agents that inhibit membrane pore formation. Pharmaceutical preparations of agents that inhibit membrane pore formation by protein toxins can be administered orally, by topical application, injection at the site of infection, and as an inhalation aerosol. The agents that inhibit membrane pore formation by bacterial protein toxins can be administered in the presence of antibiotic and antitoxin.

Bacterial infections characteristic of *Corynebacterium diphtheriae, Pseudomonas aeruginosa, Bacillus anthracis, Staphylococcus aureus*, Clostridia and other bacteria that produce membrane pore forming toxins, can be treated using the methods of the invention.

Bacterial toxins that form pores in membranes and for which the agents that inhibit membrane pore formation of the invention would be effective include diphtheria toxin, pseudomonas exotoxin, anthrax toxin, botulinum toxin, tetanus toxin, streptolysin O, aerolysin and S. aureus α-hemolysin (also called α-toxin), and the like. These toxins are similar because they all insert into membranes by exposing a hydrophobic site, and they act via a mechanism whereby the toxin enters the cytoplasm of cells to manifest its toxic activity. See, for example, Tobkes et al, *Biochemistry* 24, 1915–1920 (1985); Menestrina et al. *Biophys. J.* 60, 1388–1400 (1991); Blaustein et al. *Proc.Natl.Acad.Sci. USA* 86, 2209–2213 (1989); Hoch et al., *Proc.Natl.Acad.Sci. USA* 82, 1692–1696 (1985); Lesieur et al. *Molecular Membrane Biology* 14, 45–64 (1997); Valeva et al. *Biochemistry* 36, 13298–13304 (1997); London, *Molecular Microbiology* 6, 3277–3282 (1992); and Bayley, *Current Biology* 7, R763–R767; which are herein incorporated by reference. Bacterial toxins such as these are susceptible to treatment by the methods of the invention.

In another embodiment, the invention is a method of treating Pseudomonas aeruginosa infection in cystic fibrosis patients by administering to a subject in need of such treatment an agent that inhibits the pore formation in membranes characteristic of Pseudomonas exotoxin. The agents that inhibit membrane pore formation used can be molecules that have been selected to be effective at inhibiting pore formation by Pseudomonas exotoxin. Preferably the agent is delivered directly to the lungs of the patient in the form of an inhalation aerosol.

In order to allow more efficient entry into cells of those agents that inhibit membrane pore formation by bacterial protein toxins which carry charged groups, the agents can be generated upon hydrolysis when the agent is trapped in a cell. In this procedure, the charged group (carboxyl) is administered in uncharged form as an ester, which is then hydrolyzed by intracellular processes to the charged carboxyl group generating the active anionic species. The agents can thus be delivered in the form of precursor molecules in which membrane pore inhibitors are generated from their esters upon entrance into cells.

In yet another embodiment, the invention provides a method for reducing tissue damage associated with a bacterial infection by administering to a subject in need agents that inhibit pore formation by bacterial toxin in membranes.

Enveloped animal viruses use a mechanism of entry into cells in which viral fusion proteins interact with target membranes of the host, fusing the virus membrane and cell membrane and thereby allowing the virus to infect cells. Conformational changes of these fusion protein cause hydrophobic sites to becomes exposed so that penetration of the membrane of target cells and fusion with the cell membrane enable the virus to reach the cytoplasm. This mechanism is an important step in infection by viruses such as influenza, human immunodeficiency virus (HIV), tick borne encephalitis virus and viruses in the paramyxo, toga and orthomyxo classes. See, for example, Rey et al. *Nature* 375, 291–298 (1995); White et al. *Quarterly Reviews of Biophysics* 16, 151–195 (1983). Inhibitors of bacterial toxin pore formation could provide a starting point for the development of small molecule drugs for treatment of viral infections, because the first stage of membrane penetration by viruses and bacterial toxins is similar (London, 1992; White et al, 1983). In both cases, exposure of a hydrophobic site is the first step in membrane integration.

Another embodiment of the invention treats bacterial or viral infection by administering to a human or animal subject in need of treatment, agents that inhibit the interaction with the membranes of hydrophobic exposed groups from bacterial and viral proteins that are associated with the virulence of these bacteria or viruses. A common physical mechanism underlies the of action of all these proteins. In order to infect cells, they must undergo changes in structure that involve exposure of hydrophobic sites (sites with the capacity to interact with lipids or hydrocarbon bearing groups) (White et al, 1983). This embodiment of the invention is useful for all of the bacteria and viruses described above.

The following examples are provided to assist in a further understanding of the invention. The particular materials and conditions employed are intended to be further illustrative of the invention and are not limiting upon the reasonable scope thereof.

EXAMPLES

Materials

Anti-Cascade Blue rabbit IgG (H+L fractions) antibody (Ab) (2.5–2.8 mg/ml stock solution), Cascade blue (CB) labeled dextrans (molecular weight 3 kD, 10 kD, 70 kD, free Cascade blue probe 8-methoxy-pyrenetrisulfonic acid (MPT; molecular weight 538), N-(Lissamine rhodamine B sulfonyl)-1,2-dihexadecanoyl-sn-glycero-3-phosphoethanolamine, and triethylammonium salt (rhodamine-PE) were purchased from Molecular Probes (Eugene, Oreg.). The lipids 1,2-dioleoyl-sn-glycero-3-phosphocholine (DOPC), and 1,2-dioleoyl-sn-glycero-3-[phospho-rac-(1 glycerol)] (DOPG) were purchased from Avanti Polar Lipids (Alabaster, Ala.). The compounds Cibacron brilliant red 3B-A, Ponceau S, and fast green FGF were purchased from Aldrich Chemical Company [Milwaukee, Wis.]. Cibacron Blue F3G-A was purchased from Fluka Chemical [Ronkonkoma, N.Y.] and trypsin were purchased from Sigma Chemical Company (St. Louis, Mo.).

Partially purified diphtheria toxin was purchased from Connaught Laboratories (Ontario, Canada) and further purified as described in McKeever et al. *J Biol. Chem.* 257, 6923–6925 (1982), and Carroll et al. *Biochemistry* 25, 2425–2430 (1986), which are herein incorporated by reference. Toxin was stored in 15 mM Tris-Cl, 150 mM NaCl, pH 7.5, at 4° C.

Example 1: Fluorescence Measurements

Fluorescence measurements were performed on a Spex 212 fluorimeter in the ratio mode. Fluorescent samples were in either PBS (10 mM potassium $PO_4$, 150 mM NaCl, pH 7.2) or in Na acetate buffer (0.1 M acetate, 0.15 M NaCl, pH 4.5). All experiments were performed at room temperature.

The fluorescence intensity of the CB-dextrans was measured at an excitation wavelength of 385 nm and an emission wavelength of 417 nm. For MPT, excitation and emission wavelengths were 405 nm and 433 nm respectively. [The emission $\lambda_{max}$ for these compounds was the same at both pH 4.5 and pH 7.0)]. Background samples were prepared without fluorescent molecules, and the background fluorescence, when significant, was subtracted to yield the final value.

Example 2: Purification of CB-Labeled Dextrans

To obtain dextrans of relatively homogeneous size, the commercial 3 kD, 10 kD and 70 kD dextrans were fractionated using gel filtration chromatography and stored at room temperature in PBS at pH 7. The 70 kD dextran exhibited some degradation to lower molecular weight species when stored for over two weeks and was used within 2 weeks of purification.

Example 3: Entrapping Cascade Blue Labeled Dextrans Within Model Membrane Vesicles The CB-labeled dextrans (3 kD, 10 kD, or 70 kD) were trapped inside large unilamellar vesicles (LUVs) that were prepared by octyl glucoside dialysis as described in Jiang, J. X., et al. *J.Biol.Chem* 266, 24003–24010 (1991). The LUVs were composed of either 20% DOPG/80% DOPC (PG/PC), DOPC (100% PC), or 20% DOPG/30% cholesterol/50% DOPC (PG/cholesterol/PC) (mol/mol) and contained 0.02% rhodamine PE as a fluorescent marker. Dialysis tubing with a molecular weight 1000 cutoff was used. Prior to dialysis the lipid concentration was 10 mM. The lipid concentration was followed by measuring the fluorescence of the fluorescent marker incorporated into the lipid. Dextran concentration was monitored to determine trapping efficiency. Initial dextran concentrations were approximately 0.03 $\mu$M. (Dextran concentrations were determined using a CB fluorescence vs. concentration curve.) Free dextran was separated from vesicle trapped dextran by filtration on a Sepharose 4B-CL gel filtration column (0.5 cm×40 cm) at room temperature. Samples were eluted from the column with PBS (pH 7.2), and the fractions containing lipid were pooled.

Cascade blue labeled dextran containing vesicles (DCVs) were stored in PBS (pH 7.2) buffer at room temperature, and remained entrapped inside the LUVs for about 2 weeks.

Since MPT leaks spontaneously from vesicles, MPT-containing vesicles were made with the same initial trapping protocol, but in the dialysis step a concentration of MPT equal to that in the sample was included in the external dialysis buffer. Once vesicles were formed the free MPT was separated from trapped MPT using the Sepharose 4B-CL column, and the vesicles containing MPT were used within 24–48 h. As a further control, leakage was determined by the amount of quenching observed in trapped MPT samples in the absence of toxin.

Example 4: Measuring Dextran Leakage

This example describes the assay that was used to measure pore formation by protein toxins. An aliquot (25–45 $\mu$l) of vesicles with entrapped CB-labeled dextran or MPT was added to 150 µl of pH 4.5 acetate buffer (0.1 M NaOAc 0.15 M NaCl) at room temperature. Then small aliquots (2.5–10 µl) from PBS diluted stock solutions of toxin with various concentrations were added. Samples were incubated for 30 min and then the volume was increased to 500 µl with pH 4.5 acetate buffer. The final lipid concentration was 200 µM and the final pH 4.5. Next, CB fluorescence was measured followed by addition of excess anti-CB antibody (Ab), i.e. sufficient to obtain maximal quenching (2–5 µl of a 2.5–2.8 mg/ml stock solution). The fluorescence was remeasured after 5 min. The percent quenching was calculated as follows: [1-{(fluorescence+Ab)/(fluorescence−Ab)}]× 100%, and then percent of maximum quenching was calculated by dividing the percent quenching by the amount of quenching obtained in the presence of enough octyl glucoside (10 µl of a 200 mg/ml stock solution in PBS) to disrupt the vesicles and thereby release all entrapped molecules. Control experiments showed octyl glucoside did not interfere with quenching of CB-dextrans in solution.

Example 5: Diphtheria Toxin Pore Formation in the Presence of Agents that Inhibit Membrane Pore Formation Pore formation was assayed using the dextran leakage method described in Example 4. FIG. 1 illustrates the leakage of MPT and three different sized CB-dextrans from LUVs as a function of toxin concentration. Quenching for each of the fluorescent reporter groups is indicated in FIG. 1 by the symbols: (+) MPT, (Δ) 3 kD CB-dextran, (o) 10 kD CB-dextran and (□) 70 kD CB-dextran. At low concentrations of toxin only the small molecule MPT is quenched demonstrating release from the dextran containing vesicles. MPT release reached approximately 60% maximal quenching at 0.5 µg of toxin. As the amount of toxin was increased, the 3 kD dextran began to be released reaching about 90% quenching at 5.0 µg of toxin. The 10 kD dextran began to be released at even higher concentrations of toxin reaching approximately 50% quenching at 10 µg of toxin, the highest quantity of toxin used in these assays. This indicates that the size of the pores increase as the amount of toxin increases.

At higher protein concentrations, where the maximal amount of 3 kD dextran was released, the smaller MPT molecule was released to a lesser degree than the larger 3 kD CB-dextran. This surprising result indicated that diphtheria toxin pore formation was inhibited by the MPT molecule.

Example 6: Inhibition of Membrane Pore Formation Different Agents

FIG. 2 illustrates the inhibition of diphtheria toxin induced membrane pore formation by target agents (i.e. Cibacron Red, Cibacron Blue, Ponceau S and Amaranth). Experiments were performed as described in example 4, except for the presence of the different inhibitors of membrane toxin pore formation. The inhibitor, in this example, was added prior to the addition of toxin. Quenching for each of the fluorescent reporter groups in the presence of 10 µM inhibitor are indicated by the symbols: (+) MPT, (Δ) 3 kD CB-dextran, (o) 10 kD CB-dextran. Inhibition of pore formation by whole diphtheria toxin can best be illustrated at a single amount of toxin.

Figure 2A:
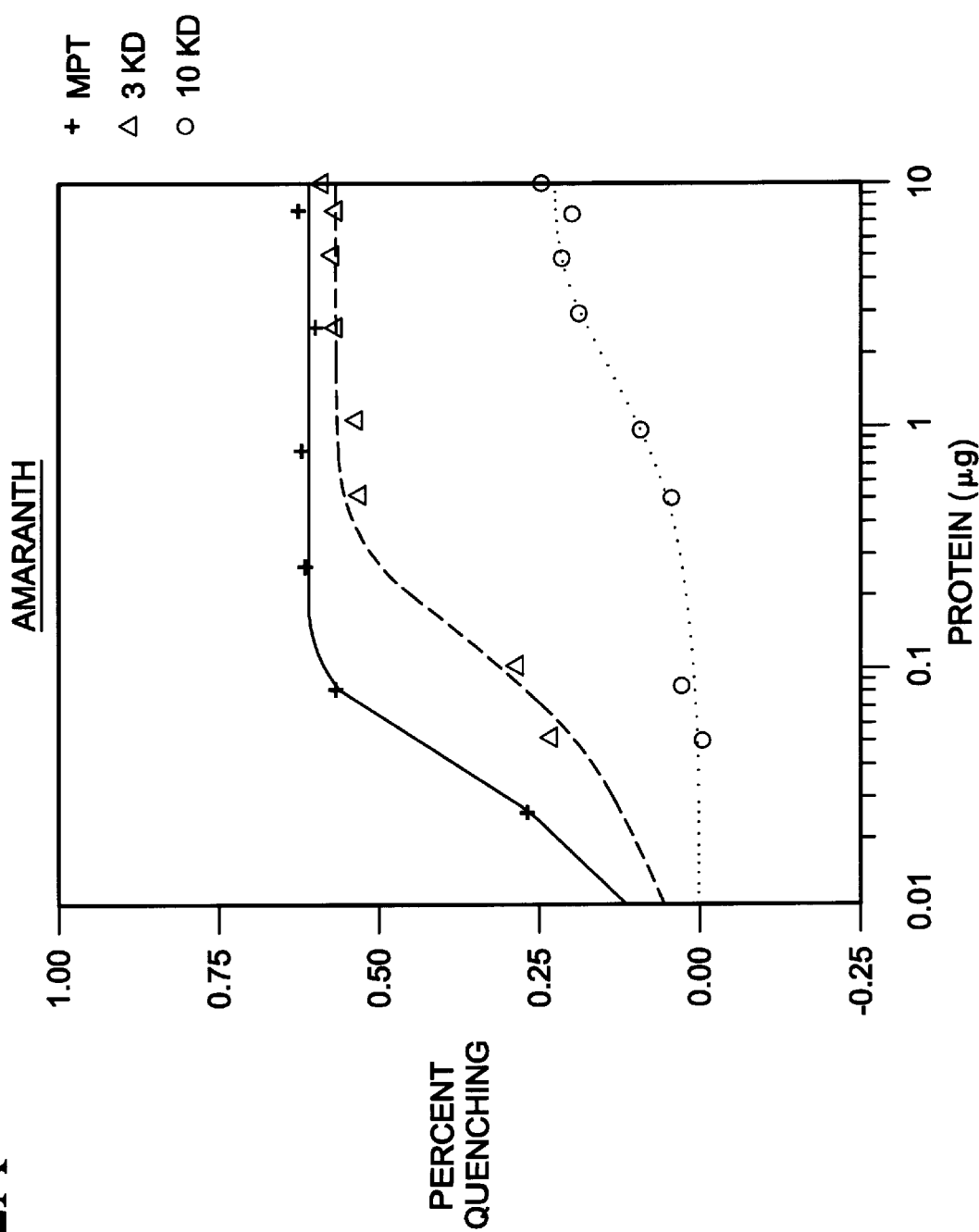
FIG. 2 describes the inhibition of diphtheria toxin induced membrane pore formation by target agents.

FIG. 2A shows that amaranth is a weak inhibitor of membrane pore formation. At 1.0 µg of toxin, quenching of the fluorescence of the 3 kD dextran was about 50%. This can be compared to the about 75% release shown in FIG. 1 at 1.0 µg of toxin in the absence of target agent. This demonstrates about 30% inhibition in the amount of 3 kD dextran released from the dextran containing vesicles.

Figure 2B:
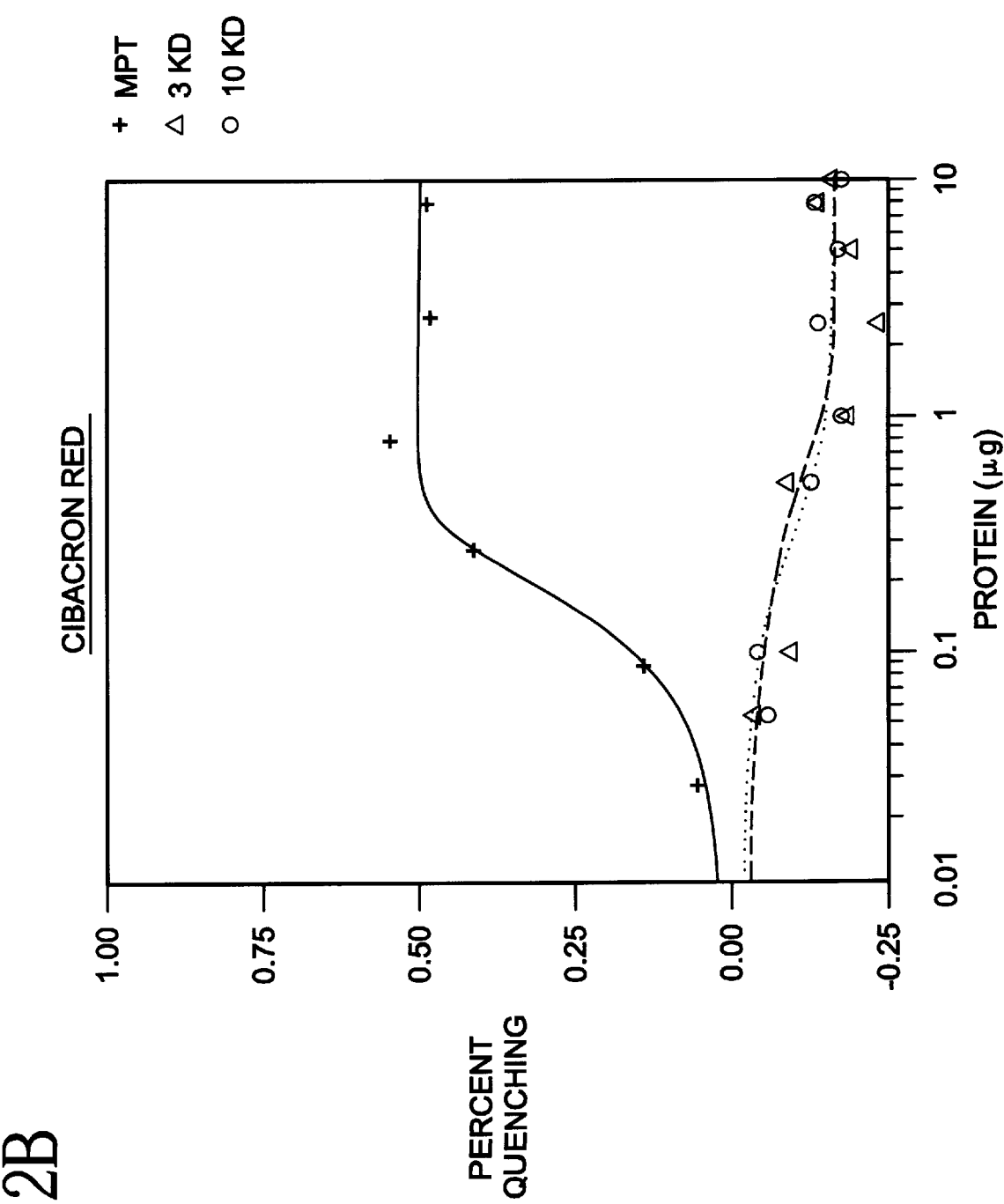

FIG. 2B shows inhibition of membrane pore formation in the presence of Cibacron Red. Cibacron Red exhibits strong inhibition as can be seen from FIG. 2B where, for example, the release of 3 kD dextran is completely inhibited at 1.0 µg of toxin. This is demonstrated by the complete lack of quenching of the 3 kD dextran resulting in 0% quenching and 100% inhibition of 3 kD dextran release.

Figure 2C:
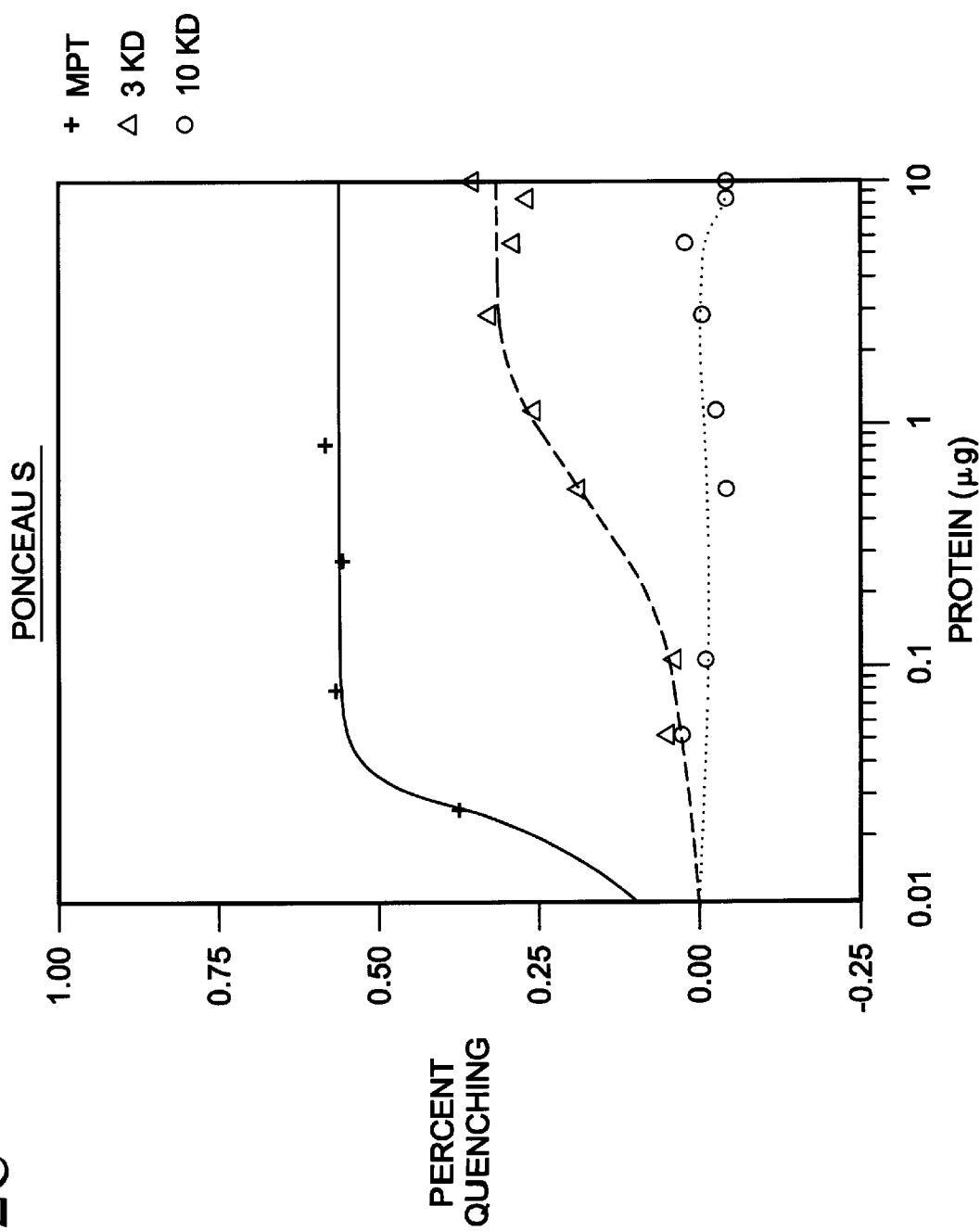

FIG. 2C shows moderate inhibition of pore formation in the presence of Ponceau S which, for example, gave about 25% quenching of the 3 Kd dextran at 1.0 µg of toxin resulting in about 67% inhibition of pore formation.

Figure 2D:
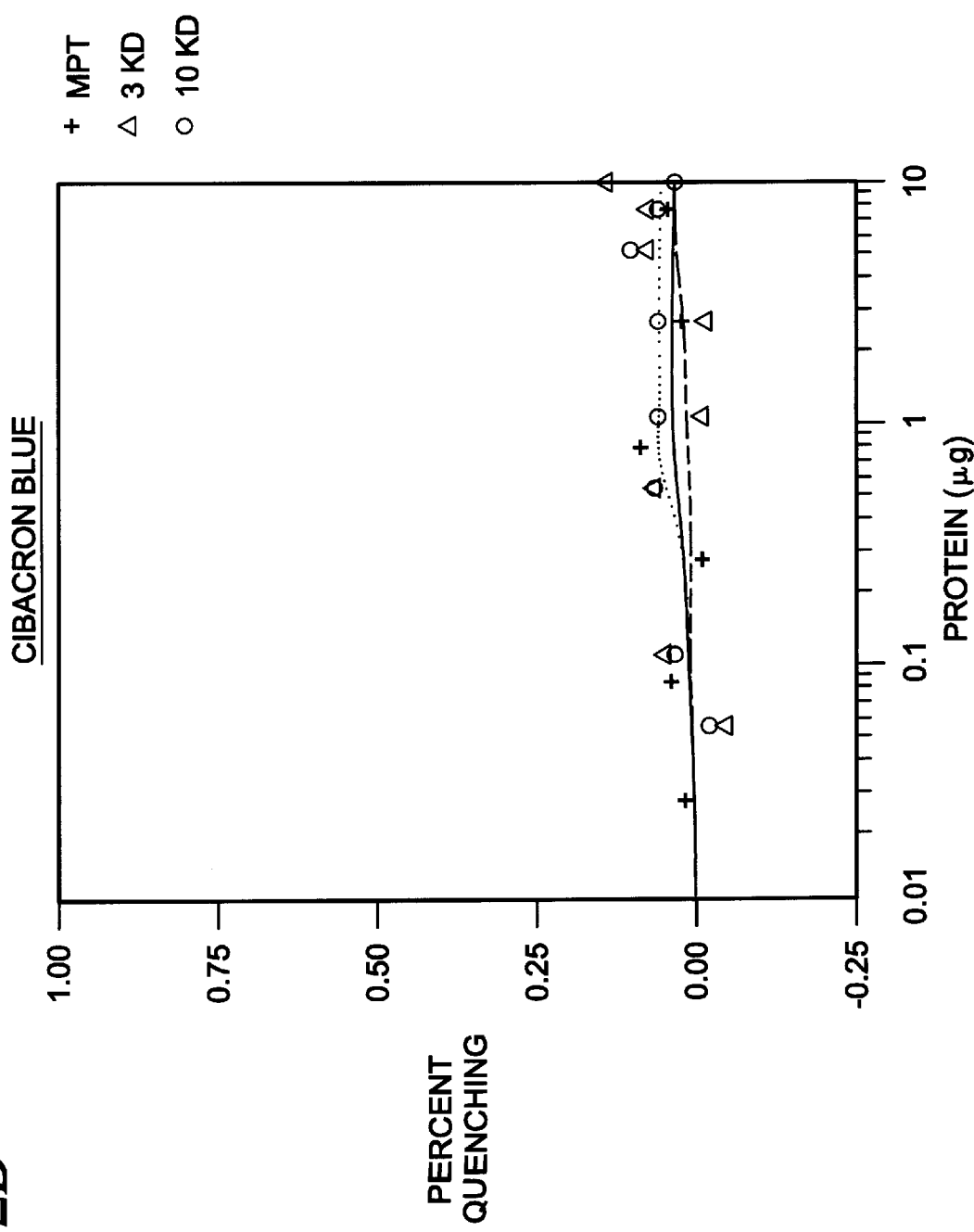

Strong inhibition was observed in the presence of Cibacron Blue where 0% quenching for all the dextrans at 1.0 µg of toxin was found. This is shown in FIG. 2D, where it can be seen that pore formation by the toxin protein was completely inhibited.

Example 7: Demonstration that Inhibitor Mechanism of Action Does Not Involve the Catalytic Domain of Diphtheria Toxin Upon removal of the catalytic site, the compounds of the invention were found to still be effective at inhibiting pore formation by the toxin. Therefore, the membrane pore inhibiting agents bind to a site other than the catalytic site of diphtheria toxin to inhibit membrane pore formation (under conditions in which diphtheria toxin forms pores in membranes).

Pore formation in the absence of the catalytic domain of the toxin was studied using the single domain of the toxin denoted the transmembrane domain or T domain. The T domain of diphtheria toxin lacks both the catalytic domain of the toxin (which contains the catalytic site) and the receptor binding domain of the toxin. The T domain has been shown to form pores in membranes similar to the pores observed for the entire toxin molecule. See, for example, Silverman J. A. et al. *J. Membrane Biol.* 137, 17–28 (1994).

Figure 3:
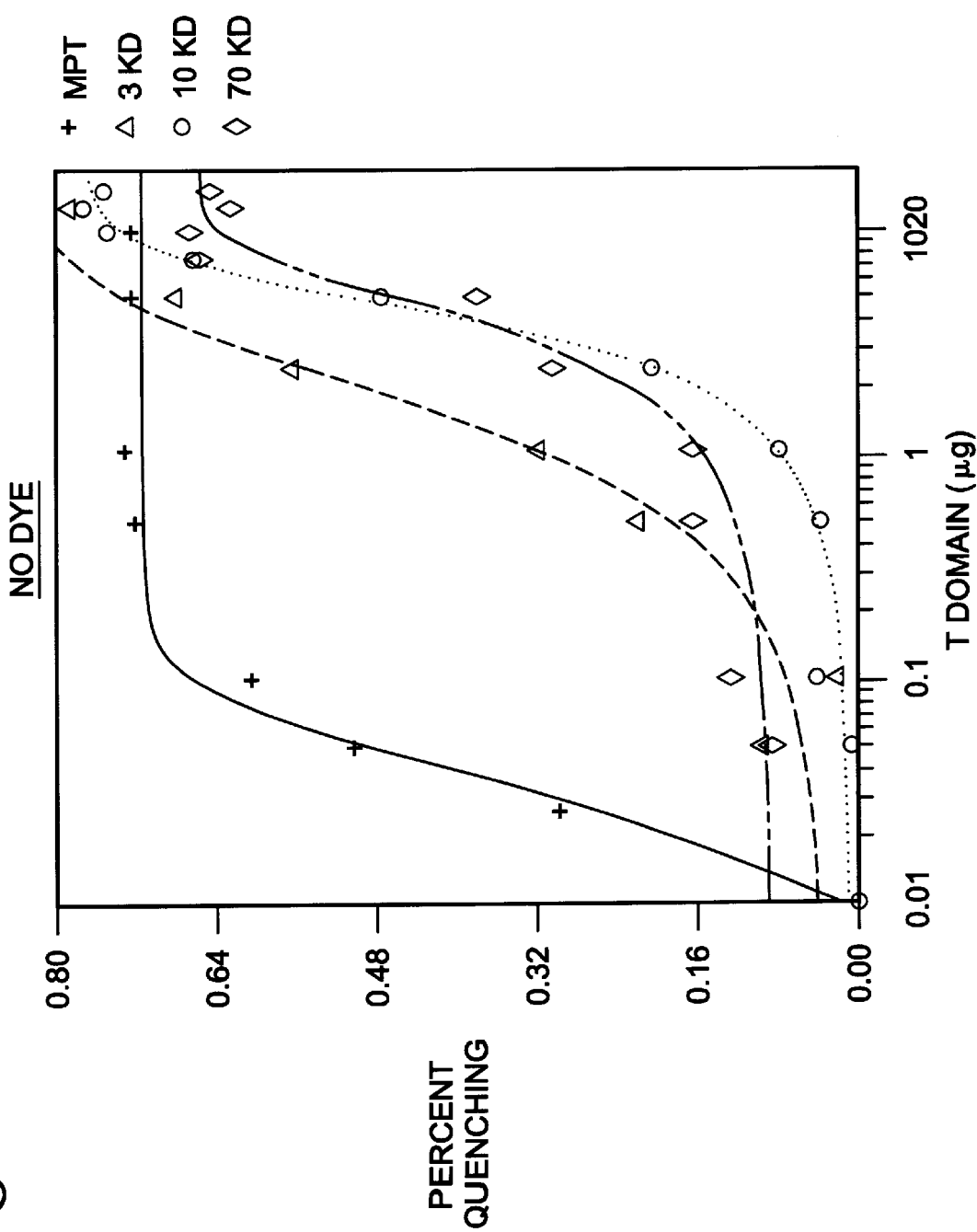
FIG. 3 describes the leakage of molecules of different sizes through pores made by the T-domain of diphtheria toxin as assessed by the quenching of fluorescence when the molecules leak out.
Figure 4A:
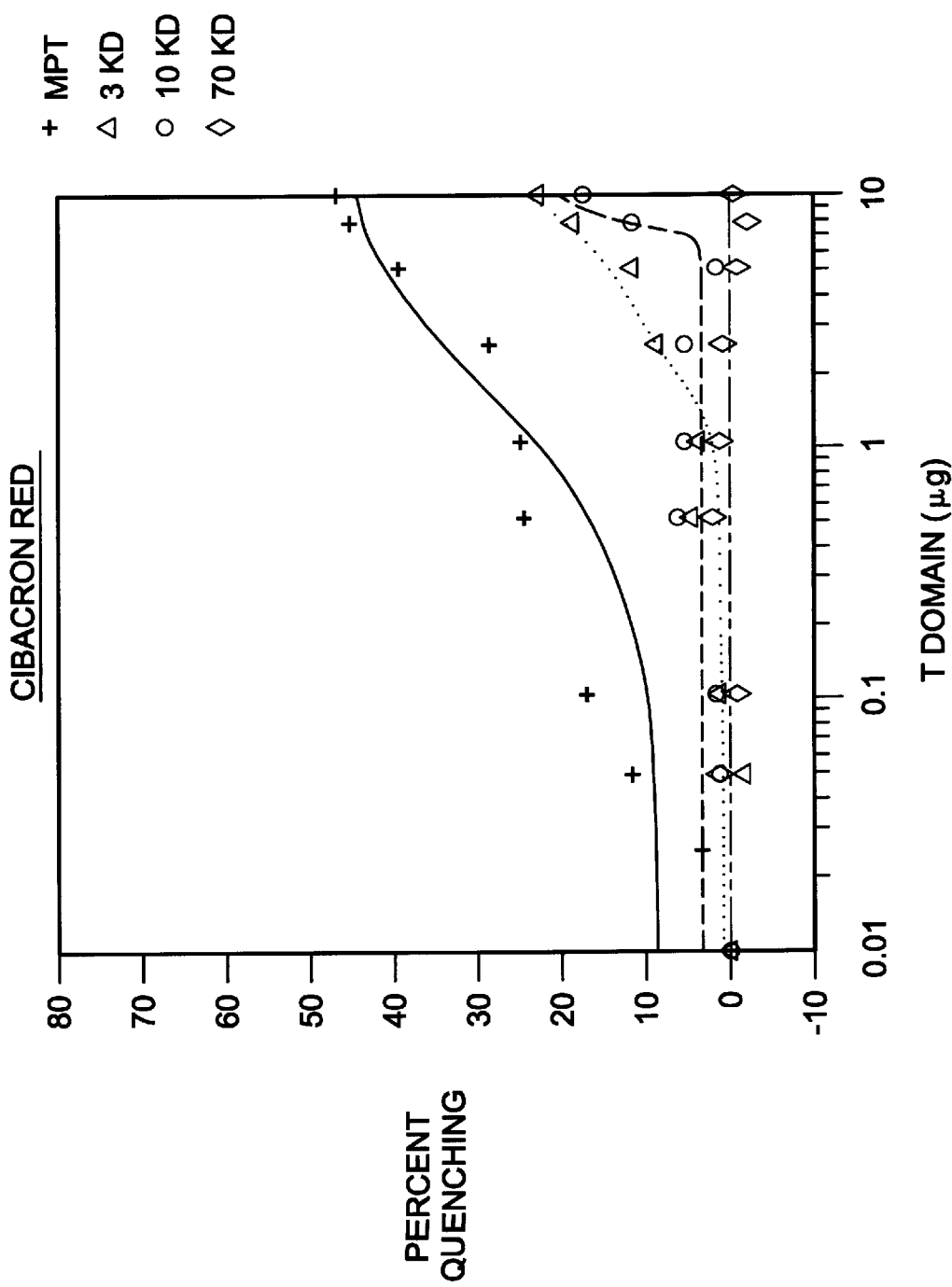
FIG. 4 describes the inhibition of diphtheria toxin T-domain induced membrane pore formation by target agents.
Figure 4B:
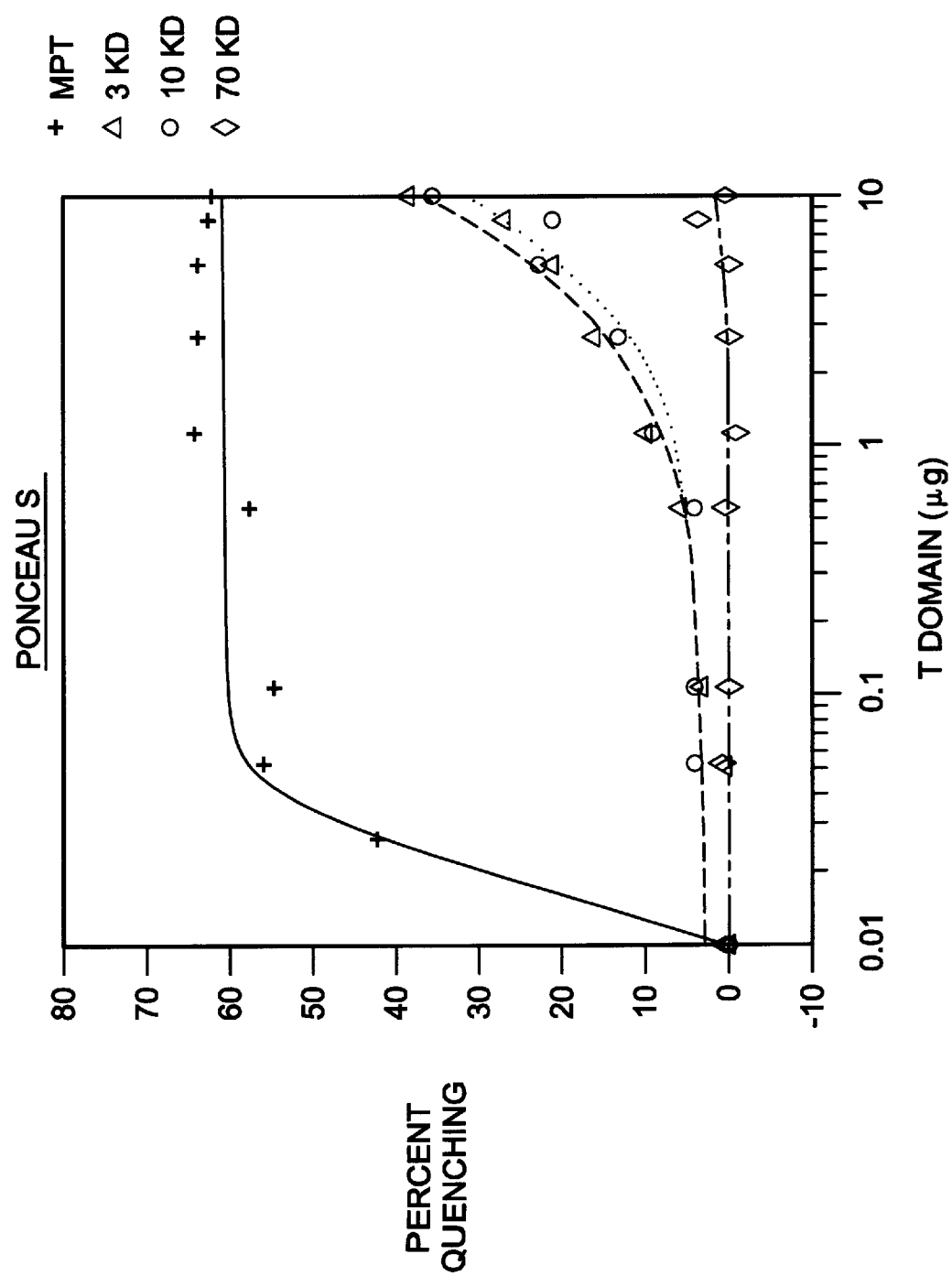
Figure 4C:
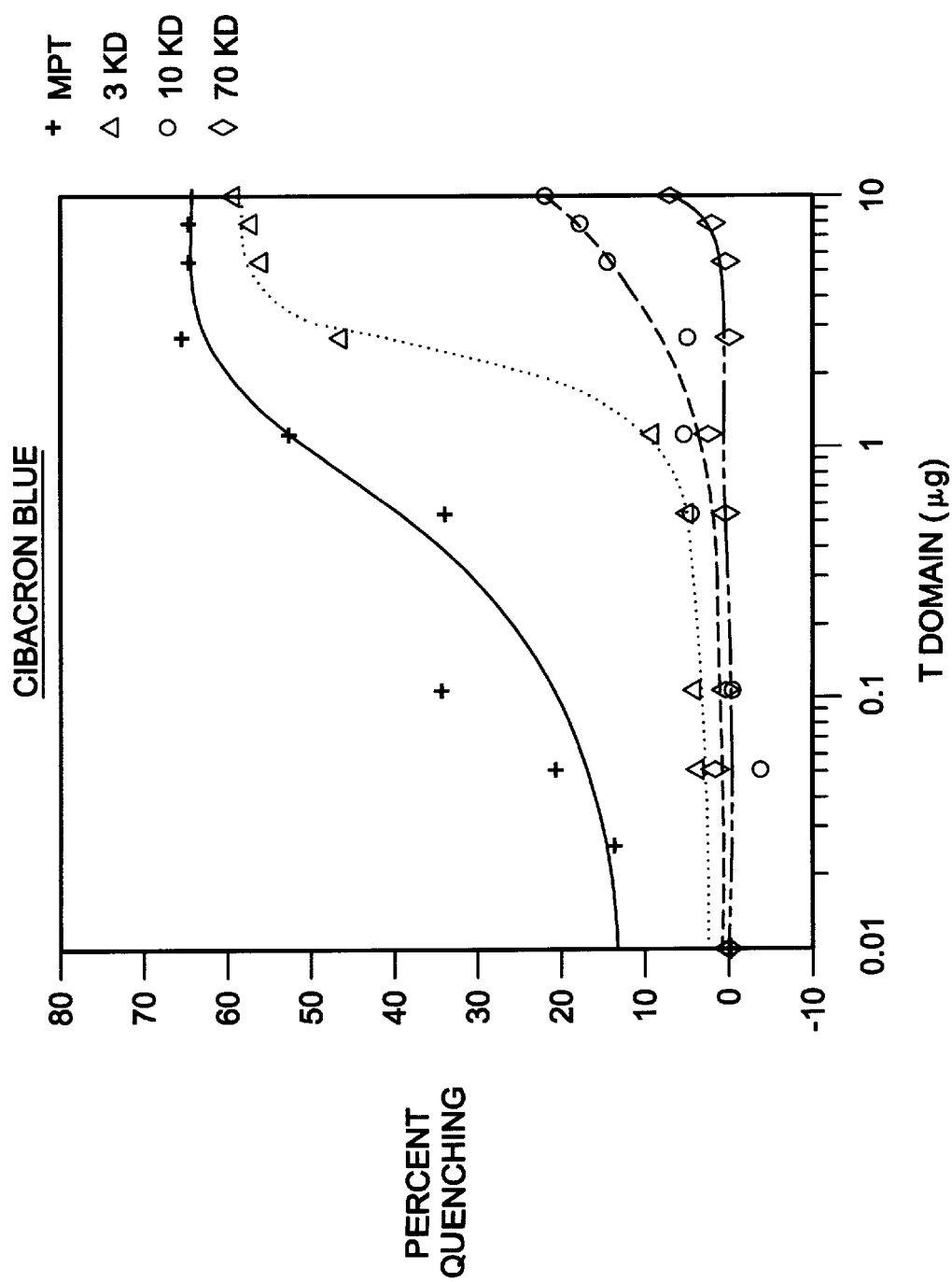

Experiments were performed as in Example 6 except that isolated T domain was used in the experiments instead of the whole toxin protein. The percent quenching of MPT and the CB-dextran fluorescence was used to determine inhibition of membrane pore formation in the presence of Ponceau S, Cibacron Blue and Cibacron Red. Quenching for each of the fluorescent reporter groups in the presence or absence of 10 µM inhibitor are indicated, for FIGS. 3 and 4, by the symbols: (+) MPT, (Δ) 3 kD CB-dextran, (o) 10 kD CB-dextran and (◊) 70 kD CB-dextran. In the absence of inhibitor, the 3 kD dextran was quenched about 70%, in the presence of about 5 µg of T domain, indicating the presence of pores in the membrane of sufficient size for the passage of a 3 kD CB-dextran from the vesicles (FIG. 3). FIG. 4A shows that for about 5 µg of T-domain in the presence of Cibacron Red, the 3 kD dextran was quenched about 9% indicating strong inhibition (87%) of membrane pore formation. FIG. 4B shows that for about 5 µg of T-domain, strong inhibition of membrane pore formation was also observed in the presence of Ponceau S. This is demonstrated by the about 20% quenching observed for the 3 kD CB-dextran which indicated strong inhibition (about 70%) of membrane pore formation by Ponceau S. FIG. 4C shows, again for 5 µg of T-domain, that somewhat less inhibition of T domain membrane pore formation (around 22%) was observed in the presence of Cibacron Blue.

What is claimed is:

1. A method for identifying antimicrobial agents which inhibit bacterial toxin membrane pore formation, comprising:

contacting a membrane pore-forming toxin protein with a target agent in the presence of a membrane under conditions in which the toxin protein spontaneously forms pores in the membrane; measuring the extent of pore formation in the membrane; and comparing the extent of membrane pore formation to that obtained in the absence of the target agent, wherein at least 10% inhibition of membrane pore formation by the target agent constitutes identifying an antimicrobial agent.

2. A method according to claim 1, wherein the membrane comprises biological molecules.

3. A method according to claim 2, wherein the membrane is in the form of a vesicle.

4. A method according to claim 3, wherein the extent of pore formation is determined by measuring the passing of a reporter group through the membrane.

5. A method according to claim 4, wherein the reporter group is fluorescent and pore formation is determined by the quenching of the fluorescent reporter upon passing through the membrane by a quencher.

6. A method according to claim 5, wherein the extent of pore formation is determined by the amount and size of the fluorescent reporter that can pass through the membrane pores.

7. A method according to claim 1, wherein the method comprises, preparing an aqueous solution, in which bacterial toxin can form pores in membranes, of phospholipid vesicles which contain fluorescent reporter in the lumen; introducing target agent and pore forming toxin to the solution and incubating; measuring the fluorescence of the solution; introducing quencher to the solution; and again measuring the fluorescence of the solution to determine the quenching of the fluorescent reporter group that has passed through the membrane, and thus assaying pore formation in the membrane.

8. A method according to claim 7, wherein the fluorescent reporter is 8-hydroxypyrene-1,3,6-trisulfonic acid labeled dextran.

9. A method according to claim 8, wherein the quencher is anti 8-hydroxypyrene-1,3,6-trisulfonic acid antibodies.

10. A method according to claim 1, wherein the method comprises, preparing an aqueous solution, in which bacterial toxin can form pores in membranes, of phospholipid vesicicles which contain quencher in the lumen; introducing target agent and pore forming toxin to the solution and incubating; introducing fluorescent reporter to the solution; and measuring fluorescence of the solution and comparing that fluorescence to fluorescence of a similar sample lacking toxin to determine the quenching of the fluorescent reporter that has passed through the membrane, and thus assaying pore formation in the membrane.

11. A method according to claim 10, wherein the fluorescent reporter is 8-hydroxypyrene-1,3,6-trisulfonic acid labeled dextran.

12. A method according to claim 11, wherein the quencher is anti 8-hydroxypyrene-1,3,6-trisulfonic acid antibodies.

13. A method for identifying antimicrobial agents which inhibit Diphtheria toxin membrane pore formation, comprising:

contacting a Diphtheria toxin protein with a target agent in the presence of a membrane under conditions in which the Diphtheria toxin protein spontaneously forms pores in the membrane; measuring the extent of pore formation in the membrane; and comparing the extent of membrane pore formation to that obtained in the absence of the target agent, wherein at least 10% inhibition of membrane pore formation by the target agent constitutes identifying an antimicrobial agent.

14. A method according to claim 13, wherein the membrane comprises biological molecules.

15. A method according to claim 14, wherein the membrane is in the form of a vesicle.

16. A method according to claim 15, wherein the extent of pore formation is determined by measuring the passing of a reporter group through the membrane.

17. A method according to claim 16, wherein the reporter group is fluorescent and pore formation is determined by the quenching of the fluorescent reporter upon passing through the membrane by a quencher.

18. A method according to claim 17, wherein the extent of pore formation is determined by the amount and size of the fluorescent reporter that can pass through the membrane pores.

19. A method according to claim 13, wherein the method comprises preparing an aqueous solution, in which Diphtheria toxin can form pores in membranes, of phospholipid vesicles which contain fluorescent reporter in the lumen; introducing the target agent and the Diphtheria toxin protein to the solution and incubating; measuring the fluorescence of the solution; introducing quencher to the solution; and again measuring the fluorescence of the solution to determine the quenching of the fluorescent reporter group that has passed through the membrane, and thus assaying pore formation in the membrane.

20. A method according to claim 19, wherein the fluorescent reporter is 8-hydroxypyrene-1,3,6-trisulfonic acid labeled dextran.

21. A method according to claim 20, wherein the quencher is anti 8-hydroxypyrene-1,3,6-trisulfonic acid antibodies.

22. A method according to claim 13, wherein the method comprises, preparing an aqueous solution, in which Diphtheria toxin can form pores in membranes, of phospholipid vesicles which contain quencher in the lumen; introducing the target agent and the Diphtheria toxin protein to the solution and incubating; introducing fluorescent reporter to the solution; and measuring fluorescence of the solution and comparing that fluorescence to fluorescence of a similar sample lacking Diphtheria toxin to determine the quenching of the fluorescent reporter that has passed through the membrane, and thus assaying pore formation in the membrane.

23. A method according to claim 22, wherein the fluorescent reporter is 8-hydroxypyrene-1,3,6-trisulfonic acid labeled dextran.

24. A method according to claim 23, wherein the quencher is anti 8-hydroxypyrene-1,3,6-trisulfonic acid antibodies.

* * * * *